United States Patent
Schlossman et al.

(10) Patent No.: US 9,308,160 B2
(45) Date of Patent: Apr. 12, 2016

(54) TERNARY AND QUATERNARY WAX-RESIN COMPOSITES FOR USE IN COSMETIC AND PHARMACEUTICAL PREPARATIONS

(71) Applicants: David Schlossman, South Plainfield, NJ (US); Edward Bartholomey, South Plainfield, NJ (US); Yun Shao, South Plainfield, NJ (US)

(72) Inventors: David Schlossman, South Plainfield, NJ (US); Edward Bartholomey, South Plainfield, NJ (US); Yun Shao, South Plainfield, NJ (US)

(73) Assignee: KOBO PRODUCTS, INC., South Plainfield, NJ (US)

( * ) Notice: Subject to any disclaimer, the term of this patent is extended or adjusted under 35 U.S.C. 154(b) by 0 days.

(21) Appl. No.: 14/181,721

(22) Filed: Feb. 16, 2014

(65) Prior Publication Data

US 2014/0235734 A1 Aug. 21, 2014

Related U.S. Application Data

(62) Division of application No. 12/410,550, filed on Mar. 25, 2009, now Pat. No. 8,679,464.

(51) Int. Cl.

| | |
|---|---|
| *A61K 8/92* | (2006.01) |
| *A61Q 1/04* | (2006.01) |
| *A61Q 1/06* | (2006.01) |
| *A61Q 1/10* | (2006.01) |
| *A61K 8/31* | (2006.01) |
| *A61Q 17/04* | (2006.01) |
| *A61K 8/81* | (2006.01) |
| *A61K 8/02* | (2006.01) |
| *A61Q 5/06* | (2006.01) |
| *A61Q 15/00* | (2006.01) |
| *A61K 8/89* | (2006.01) |

(52) U.S. Cl.
CPC ............... *A61K 8/92* (2013.01); *A61K 8/0241* (2013.01); *A61K 8/0254* (2013.01); *A61K 8/31* (2013.01); *A61K 8/8111* (2013.01); *A61K 8/922* (2013.01); *A61K 8/927* (2013.01); *A61Q 1/04* (2013.01); *A61Q 1/06* (2013.01); *A61Q 1/10* (2013.01); *A61Q 5/06* (2013.01); *A61Q 17/04* (2013.01); *A61K 2800/31* (2013.01); *A61Q 15/00* (2013.01)

(58) Field of Classification Search
CPC ......... A61K 8/92; A61K 8/922; A61K 8/927; A61K 8/0241; A61K 8/0254; A61K 8/31; A61K 8/8111; A61K 8/81; A61K 8/89; A61K 2800/31; A61K 8/00; A61K 8/02; A61K 8/18; A61Q 1/04; A61Q 1/06; A61Q 1/10; A61Q 5/06; A61Q 15/00; A61Q 17/04; A61Q 1/02; A61Q 5/12; A61Q 19/04
See application file for complete search history.

(56) References Cited

U.S. PATENT DOCUMENTS

| | | | | |
|---|---|---|---|---|
| 2,384,141 | A * | 9/1945 | Soday | ........................ 524/246 |
| 2006/0067960 | A1* | 3/2006 | Russ | .................. A61K 8/8194 424/401 |
| 2006/0134035 | A1* | 6/2006 | Zheng | ................ A61K 8/8111 424/64 |

*Primary Examiner* — Jane C Oswecki
(74) *Attorney, Agent, or Firm* — Handal & Morofsky LLC.

(57) ABSTRACT

A wax-resin composite is made by melting thermoplastic hydrocarbon resin, optionally with an antioxidant. The melted thermoplastic hydrocarbon resin and waxes are blended at a temperature sufficient to melt the waxes. After blending and melting, the blended thermoplastic hydrocarbon resin and waxes are allowed to solidify. Solidification is followed by post-processing the wax-resin composite mixture to form slabs, pastilles, flakes or other forms. A method for producing a wax-resin composite comprises at least partially solvating a thermoplastic resin in a solvent to form a resin-solvent blend. This may be done at a heat of 80-85° C. A composition of molten wax is blended with the resin-solvent blend. The resin-solvent blend and a molten wax are blended to form a wax-resin blend. This is followed by removing the solvent from said wax-resin blend.

12 Claims, 2 Drawing Sheets

TERNARY AND QUATERNARY WAX-RESIN COMPOSITES FOR USE IN COSMETIC AND PHARMACEUTICAL PREPARATIONS

CROSS REFERENCE TO RELATED APPLICATIONS

This application claims priority as a divisional under 35 U.S.C. 121 to U.S. patent application Ser. No. 12/410,550 filed on Mar. 25, 2009, entitled "TERNARY AND QUATERNARY WAX-RESIN COMPOSITES FOR USE IN COSMETIC AND PHARMACEUTICAL PREPARATIONS," which claims priority under 35 U.S.C. 119(e) to U.S. Provisional Application Ser. No. 61/044,301, entitled "COSMETIC AND PHARMACEUTICAL COMPOSITIONS COMPRISING WAX-RESIN COMPOSITES," filed Apr. 11, 2008, each of which are incorporated by reference in their entirety.

TECHNICAL FIELD

The present invention relates to a complex of a thermoplastic hydrocarbon resin processed together with a blend of waxes. In accordance with certain embodiments of the present invention, the complexes may be used in cosmetic and pharmaceutical compositions. The complex may be in the form of a ternary or quaternary composite.

Hydrocarbon-based resins have excellent adhesion that helps to improve wear. They are not used very frequently in cosmetics and pharmaceutical bases, because the adhesion translates to poor sensory properties when applied to the skin, hair, lashes and nails. It also results in an occlusive film on the skin. Kobo Products Inc. currently manufactures solutions of hydrogenated polycyclopentadiene for cosmetic use. Our invention focuses upon hydrocarbon resins derived from petroleum and does not include hydrocarbon resins produced from, for example plant derived, terpene or rosin.

SUMMARY OF THE INVENTION

The invention introduces new complexes that may be in the form of crystalline solids or which may be incorporated into suspensions which help to both facilitate incorporation of the polymer into various phases and also provide a wider range of materials for flexibility of formulation use in the end products. By ternary and quaternary composites is meant the combination of resin (e.g. Escorez polycyclopentadiene) with two or three waxes.

Though adhesion is required and is a component of long-wear products, lesser amounts of adhesion can still achieve excellent results, especially when combined and balanced with materials that are abhesive or have non-stick properties, especially waxes. The ternary and quaternary complexes are formed from the resin and wax blends. An additional component, an antioxidant, is typically included to insure stability of the matrix for odor and chemical integrity. Hydrocarbon waxes or natural waxes containing hydrocarbons have been found to modify and improve the properties of a tackifier polymer, hydrogenated polycyclopentadiene. This complex forms a hydrocarbon wax-resin composite. This material described herein can be used for cosmetic and pharmaceutical formulations to improve rub-resistance, adhesion and flexibility of the final film on the skin, hair, lashes and nails, thereby improving overall performance. Surprisingly, applicants found that even very small amounts of solid waxes significantly modified the properties of hydrogenated polycyclopentadiene. The inclusion and complexation of the wax with the polymer provided a balance between the adhesion and sensory acceptability properties mentioned above.

BRIEF DESCRIPTION OF THE DRAWINGS

The invention may be understood with reference to the drawings in which.

DETAILED DESCRIPTION OF THE PREFERRED EMBODIMENTS

Figure 1:
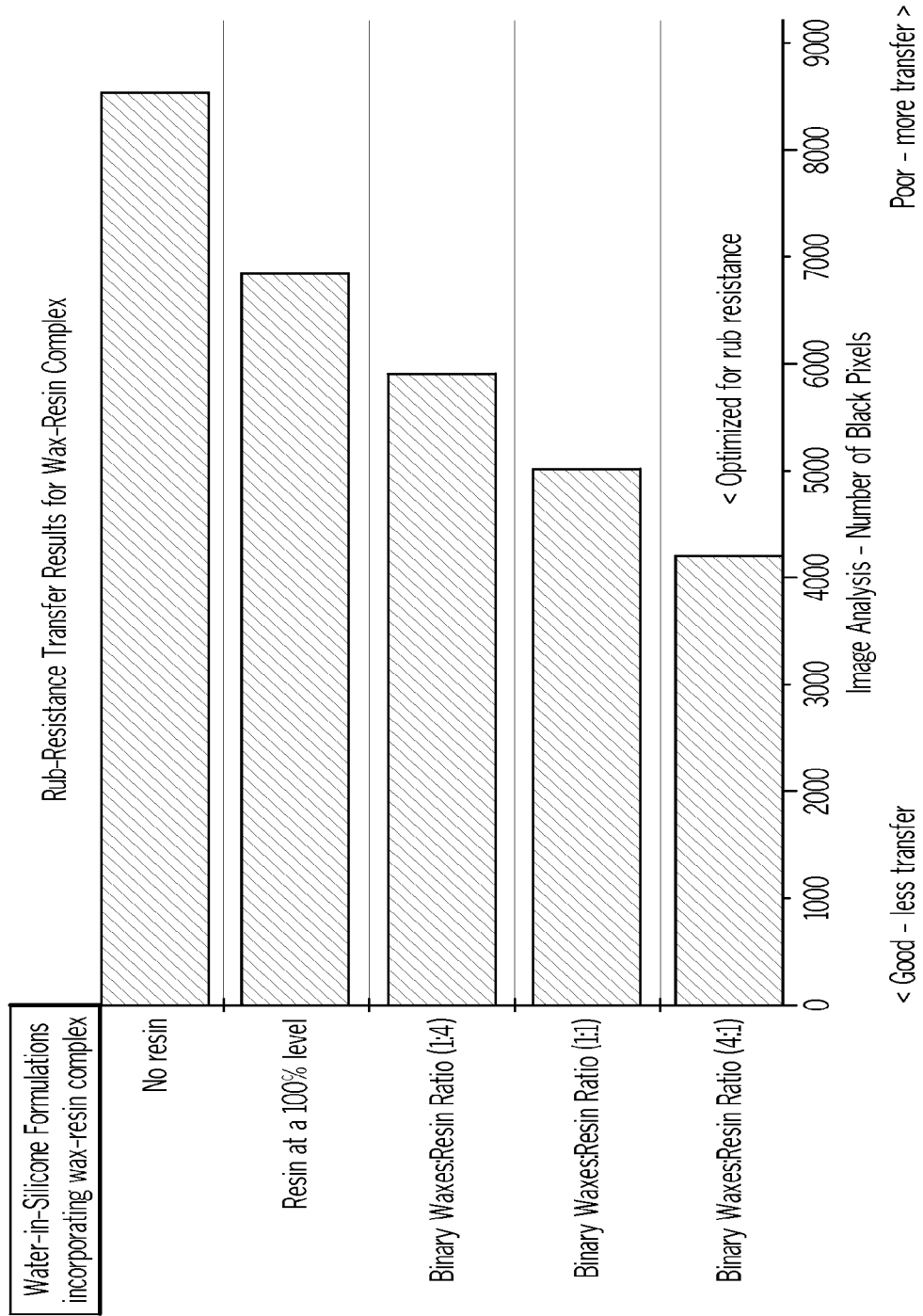
FIG. 1 is a graphical representation of rub-resistance transfer for a range of materials.

In accordance with one aspect of the present invention, the hydrocarbon resin is first partially solvated with a hydrocarbon solvent to blend the waxes and hydrocarbon resin together in a homogenous mixture. This produced clear solutions when mixed with molten wax. Blending the molten wax with the resin alone did not result in a complete solution for most blends at normal processing temperatures for the waxes. For the solvent process, the composite was heated below the softening point of the resin which is above 100° C. Plasticizing the resin with a solvent and hydrocarbon waxes, makes it possible to process the composite within normal ranges of the melting points of the waxes. Through controlled evaporation of the solvent, solid granules via crystallization and semi-solid dispersions are produced.

Another aspect of the invention includes a thermal process, whereby the temperatures can exceed 100° C. An antioxidant was included to prevent any changes in the waxes. The thermal process allows for both the formation of the composite, as well as direct post-processing of the complex into pastilles and other shapes.

Controlled temperatures result in semi-transparent to transparent solids, in the form of pastilles and other shapes. Equipment other than those listed in the basic lab process and described in this document may also be used to produce these complexes. A Processall or rotary evaporators, etc. may also be used.

According to specific embodiments, the composition may comprise at least two to three different waxes in combination with the hydrogenated polycyclopentadiene. One wax may be a hydrocarbon wax such as a polyethylene wax, a synthetic wax or a petroleum type wax. They may be linear or branched. The second wax may be a natural wax which contains hydrocarbons or has a hydrocarbon-like structure or component to it, such as carnauba wax. Natural waxes improve the affinity of the inventive end product to a variety of carriers. The third may be selected from any of the classes of waxes: hydrocarbon, synthetic, petroleum or natural.

The complex can be used for cosmetic and pharmaceutical compositions, such as emulsions (oil-in water, water-in-oil, as well as silicone, hydrocarbon and ester emulsions, both volatile and non-volatile), hot pour, anhydrous, powders, sunscreens, delivery patches, ointments, encapsulation, surface-treatments, binders and general coatings to improve wear. The complex may be used in either the internal or external phase or both phases simultaneously. The invention can also improve the stability of films on the skin, hair, nails and lashes for cosmetic and pharmaceutical compositions for products such as lipstick, mascara, nail polish, eye shadow, sunscreens, etc.

These wax-resin complexes may be added to emulsions both prior to emulsification and also post emulsification. They may be added to other product forms such as anhydrous systems and powders during the initial stages of processing or upon letdown and during cooling or during the finishing stages of the product.

Composites create a synergism producing material properties unavailable from the individual constituent materials. By solubilizing the adhesive hydrocarbon resin together with blends of waxes and an antioxidant, a number of benefits may be realized in accordance with certain aspects of the present invention.

First, the complex facilitates the incorporation of the high melting hydrocarbon resins (softening point 85° C. to 125° C.) into cosmetic and pharmaceutical vehicles. Hydrocarbon resins can take significantly long periods of time to completely solubilize even when using high shear and high temperature. By capturing the resin within a compatible wax matrix, the time to solubilize the resin may be reduced to minutes using only low shear. When heated, the wax crystals melt within the resin matrix and disrupt the polymer structure enough to allow solubilization within a solvent. This results in a solubilized complex that can be used more readily in production for cosmetics and pharmaceuticals than the polymer itself and with better performance.

In addition to this, abhesive (or non-stick) properties of binary and ternary wax blends can balance the strong adhesion of the hydrocarbon resin, resulting in a material matrix that optimizes adhesion for application to the skin, hair, lashes, lips and nails.

Third, the use of binary and ternary blends of waxes can reinforce the hydrocarbon resin thereby improving rub-resistance. The resulting film may be tougher and more resistant to abrasion. Water-resistance may be increased when the complex is incorporated into formulations due to the hydrophobic nature of the components.

A fourth benefit is that flexibility and breathability of the hydrocarbon resin may be improved by the addition of binary and ternary wax blends which alter the structure of the resin. The addition of waxes to the resin increases both ductility and breathability of the formed film.

Finally, overall physical stability of cosmetic and pharmaceutical products may be improved for both anhydrous suspensions and emulsions, as the matrix of the waxes and hydrocarbon resin combine to envelope the solvents or external phases of the systems. It can also improve stability when used in the internal phase of an emulsion.

Composites are engineered materials and are generally made of two or more components. Composite materials, in accordance with the invention are created by combining a matrix with another material for reinforcement. The matrix material surrounds and supports the reinforcement materials binding them. The reinforcements impart their special mechanical and physical properties to enhance the matrix properties. For example, one may incorporate fibers. The fiber can be a silica, graphite, or a polymer. A polymer that may be used for this purpose is polyethylene or polyethylene-like materials.

However, even when the polyethylene is not elongated like a fiber and is more plate-like or crystalline, we have found that reinforcement still occurs in our invention, though of a somewhat different nature with more flexibility. Compatibility is key to reinforcing the matrix and so hydrocarbon waxes or hydrocarbon-containing waxes provide good functionality with hydrocarbon resins. The compatibility of the mixtures can be determined using cloud point measurements. The lower the cloud point temperature, the better the compatibility.

For composites, the matrix may be a thermoset or thermoplastic material. An example of a thermoset is an epoxy resin. However, polymers can also be used for this purpose. An example of thermoplastic polymers is a polyimide.

For certain aspects of the present invention a thermoplastic polymer, hydrogenated polycyclopentadiene, functions as the matrix.

The waxes for use in the present invention should crystallize or freeze prior to or together with the setting of the resin. The waxes should be compatible with the resin. If the melting point of the wax is too low, the resin will crystallize first and then be surrounded by the wax which melts at a lower temperature. The waxes should be optimized with the hydrocarbon resin for co-crystallization and reinforcement of the matrix. This results in the production of transparent solids, such as semi-transparent, crystalline pastilles. These pastilles or other forms may also incorporate colors, pigments or dyes which have been pre-dispersed or solubilized as part of the overall complex.

Chain molecules of many natural and artificial polymers are arranged in a way which is at least partially crystalline. Polyethylene chains are arranged in a zigzag pattern which results in a large reduction of the stiffness of the polymer. Before the plastic can break, many of the crystals have to unfold making it very tough. One example of the invention is the use of polyethylene wax in combination with another wax to form the composite with the matrix, hydrogenated polycyclopentadiene. The addition of the polyethylene to the complex helps to improve the overall resistance of the film to abrasion.

The composition contains, for example, a solid, crystalline or semi-crystalline phase of: polyethylene or a petroleum wax or a synthetic wax, a hydrocarbon resin, and a natural wax such as carnauba or candelilla wax, also containing significant amounts of hydrocarbons. In this preferred composition, the wax co-crystallizes or either crystallizes just slightly before the $T_g$ (glass transition temperature) of the resin, thus forming a crystalline or semi-crystalline phase dispersed throughout a continuous matrix (hydrocarbon resin). The inventive compositions may employ four components.

As a first component, hydrocarbon thermoplastic resins may be used. The organic resins utilized herein can be one or more of a broad group of materials which are compatible at elevated temperatures at the desired ratio with the waxes. By "elevated temperatures" is meant the temperature of manufacture which normally is at least above the melting point of the highest-melting component of the waxes. The melting points (softening point) or melting ranges of the preferred thermoplastic resins is normally in the range of about 50° to about 150° C., preferably between about 85 to about 115° C. In accordance with certain embodiments, the resins are selected to have a melting point close to the melting point of the polyethylene, synthetic wax or hydrocarbon wax or other waxes in the complex. The preferred resins belong to a class of materials referred to in industry by the term "hydrocarbon resins". Hydrocarbon resins are defined by the Kirk-Othmer Encyclopedia of Chemical Technology, Second Edition, Volume 11, John Wiley & Sons, New York, N.Y., 1966, page 242 et seq., as the readily thermoplastic polymers of low molecular weight derived from coal-tar fractions, from deeply cracked petroleum distillates, and from turpentine. These hydrocarbon resins (which are not hydrocarbon in the strictest sense of the term, since they may contain minor amounts of oxygen or other elements occurring in these natural materials) generally have a molecular weight of about 300 to about 1,200, preferably about 300 to about 900. Preferred resins are primarily derived from dicyclopentadiene streams (DCPD).

Aromatic streams can also be used to modify DCPD. Both streams are byproducts of the commodity olefins ethylene and propylene.

Typical hydrocarbon resins useful in the practice of the invention include hydrogenated hydrocarbon resins. From the standpoint of obtaining high compatibility with polyethylene wax and the other waxes, the "Escorez" resins (Exxon Mobil Chemical Company) have been found to be particularly suitable. These hydrocarbon resins are hydrogenated polycyclopentadienes that meet requirements for food packaging including low color and low odor. Escorez 5400 and 5415 are examples of this resin. They are generally used in hot melt adhesives for coating food packaging and other varied uses, but they are also of value for cosmetics and pharmaceuticals. The present invention addresses many of the issues associated with their potential use for cosmetic and pharmaceutical applications.

The polymers of cyclopentadiene are readily produced in known manner by the polymerization of cyclopentadiene or polymers thereof, for example, by heating over an extended period at temperatures of about 150° C. to 250° C. or by the action of catalysts. In this manner, mixtures of unsaturated hydrocarbons are obtained, the carbon skeletons of which consist of a series of five-membered rings, a double bond being present in each end ring of the polymer molecules. It is of advantage for some purposes to saturate these double bonds by hydrogenation, which hydrogenation may be effected in a simple manner, for example, by a treatment with hydrogen under pressure in the presence of active nickel. Among the saturated hydrocarbons of this kind those containing two or more condensed five-membered rings are preferred for use in the resin-wax complexes.

The higher saturated polymers of cyclopentadiene, particularly the hydrogenated pentamer, are extremely useful compounds for incorporation in the resin-wax compositions. They are solids at 20° C. When mixed with waxes of natural or synthetic origin containing hydrocarbons, either a decrease or an increase in the melting point of the natural or synthetic waxes occurs depending on the polymers used and the quantitative proportions of the constituents in the mixture. Wax-resin compositions in accordance with the invention, in which the cyclopentadiene derivative is a hydrocarbon, may be produced which, in addition to the aforementioned properties, may have melting points that extend above 100° C. but may also be less than 100° C.

As a second component hydrocarbon waxes, polyethylene waxes, synthetic waxes or petroleum waxes may be used. The crystalline polyethylenes found useful in this invention are those which have a specific gravity of about 0.90 to about 0.98, preferably about 0.91 to about 0.95, as determined by the density gradient technique (ASTM Test D 1505-63E). These polyethylenes have been found to have molecular weights of about 500 to about 10,000, preferably about 1,000 to about 3,500, and exhibit an average viscosity of less than 500 cps at 140° C. (Brookfield viscometer, Model LVT). The preferred polyethylenes are highly crystalline. The term "crystalline", as used herein, characterizes those polyethylene polymers which have a definite visible crystal structure as observed through a petrographic microscope. Polyethylenes are also commonly referred to or described as waxes due to their wax-like properties.

The following is a non-limiting list of typical commercially available polyethylene polymers useful in the invention. All of these polymers are manufactured by Honeywell Personal Care and have "Asensa" commercial grade numbers or are manufactured by New Phase Technologies as Performalene or Performa V series. Polymer grades Asensa SC 220, SC 210, SC 201 810A, 820A, 1702 and SC 221 are some examples of non-emulsifiable polyethylenes. They were formerly known as 'AC' grades manufactured by Allied Chemical.

| Polymer Grade | Melt. pt. (° C.) | Density (g/cc) at 25° C. |
| --- | --- | --- |
| Asensa SC 201 | 106 | 0.92 |
| Asensa SC 210 | 101 | 0.91 |
| Asensa SC 220 | 115 | 0.93 |
| Asensa SC 221 | 115 | 0.93 |
| Asensa SC 222 | 115 | 0.93 |
| Performa V 103 | 74 | 0.92 |
| Performa V 253 | 67 | 0.92 |
| Performa V 260 | 54 | 0.90 |
| Performalene 400 | | |

Synthetic waxes such as amide waxes, ester waxes, etc., or any wax-like material which can be upgraded in accordance with this invention. The only requirements are that the hydrocarbon polymer, hydrogenated polycyclopentadiene, be compatible with the wax or wax-like material. Synthetic waxes include those disclosed in Warth, Chemistry and Technology of Waxes, Part 2, 1956, Reinhold Publishing, the contents of which are hereby incorporated by reference. The waxes most useful herein have melting points from about 55° C. to about 115° C. and are selected from the C8 to C50 hydrocarbon waxes. Synthetic waxes include long-chained polymers of ethylene with OH or another stop length grouping at the end of the chain. Such waxes include the Fischer-Tropsch waxes as disclosed in the text disclosed above at pages 465-469 and include Rosswax, available from Ross Company and PT-0602 available from Astor Wax Company or New Phase Technologies synthetic waxes. Silicone waxes may also be used. The setting time of the wax-resin composite may be reduced by increasing the concentration of a synthetic wax. The term "hydrocarbon wax" is a wax composed solely of carbon and of hydrogen. Hydrocarbon wax and oil emollients include branched and unbranched hydrocarbons such as petrolatum, microcrystalline waxes, paraffins, ceresin, ozokerite, polyethylene and the like.

As a third component, natural waxes containing hydrocarbons or hydrocarbon like structures may be used. Naturally occurring waxes or those naturally occurring and processed or chemically modified may be made into the composite for this invention. These include petroleum waxes such as paraffin wax, microcrystalline wax, etc., naturally occurring waxes such as beeswax, carnauba, candelilla, jojoba, montan, peat wax, ouricury wax, soy wax, esparto wax, rice wax, sugar cane wax, maize wax, bayberry, etc. or any wax-like material which can be upgraded in accord with this invention, such as hydrogenated castor oil. The primary requirement is that the hydrocarbon polymer, hydrogenated polycyclopentadiene, be compatible with the wax.

The waxes suitable for use in the present compositions include, but are not limited to, those selected from the group consisting of candelilla, beeswax, beeswax having free fatty acids removed (modified beeswax), carnauba, candelilla, ozokerite, ceresin, paraffin, microcrystalline waxes, and mixtures thereof. More particularly the waxes may be selected from the group consisting of microcrystalline, candelilla, modified beeswax, carnauba, ozokerite, paraffin, ceresin and mixtures thereof. Waxes such as triglycerides or glycol diesters of $C_{18}$ to $C_{36}$ fatty acids are also suitable.

As a fourth component natural waxes containing hydrocarbons or hydrocarbon-like structure and hydrocarbon waxes, such as polyethylene waxes, synthetic waxes or petroleum waxes may be used. See the discussion of the second and third components. The fourth component is inclusive of all of the above in its description referring to the second and third components.

It is within the scope of this invention to add low boiling solvents and/or plasticizers and antioxidants, as previously described. The plasticizer or flexibilizer materials lower the melt viscosity and increase flexibility. Among the suitable plasticizers are: mineral oil, soya oil, isostearyl isonananoate, and safflower oil and other oils and esters. Anti-oxidants that are preferred are tocopherols, but are not limited to these alone. The composition may contain antioxidant compounds with sterically hindered phenolic hydroxyls. An antioxidant concentrated in 7,8-dimethyltocol can be used.

Test Results for Rub Resistance

Films were created from a series of water-in-silicone/isododecane formulations containing pigments and a wax-resin composition in accordance with certain aspects of the present invention at various ratios or blends of the waxes and resin components. These films were abraded at a constant pressure and weight and then transferred to image analysis software for results. Results are shown in FIG. 1 Rub resistance demonstrates the strength and flexibility of the films incorporating the wax/resin complexes.

Test Results for Adhesion

Figure 2:
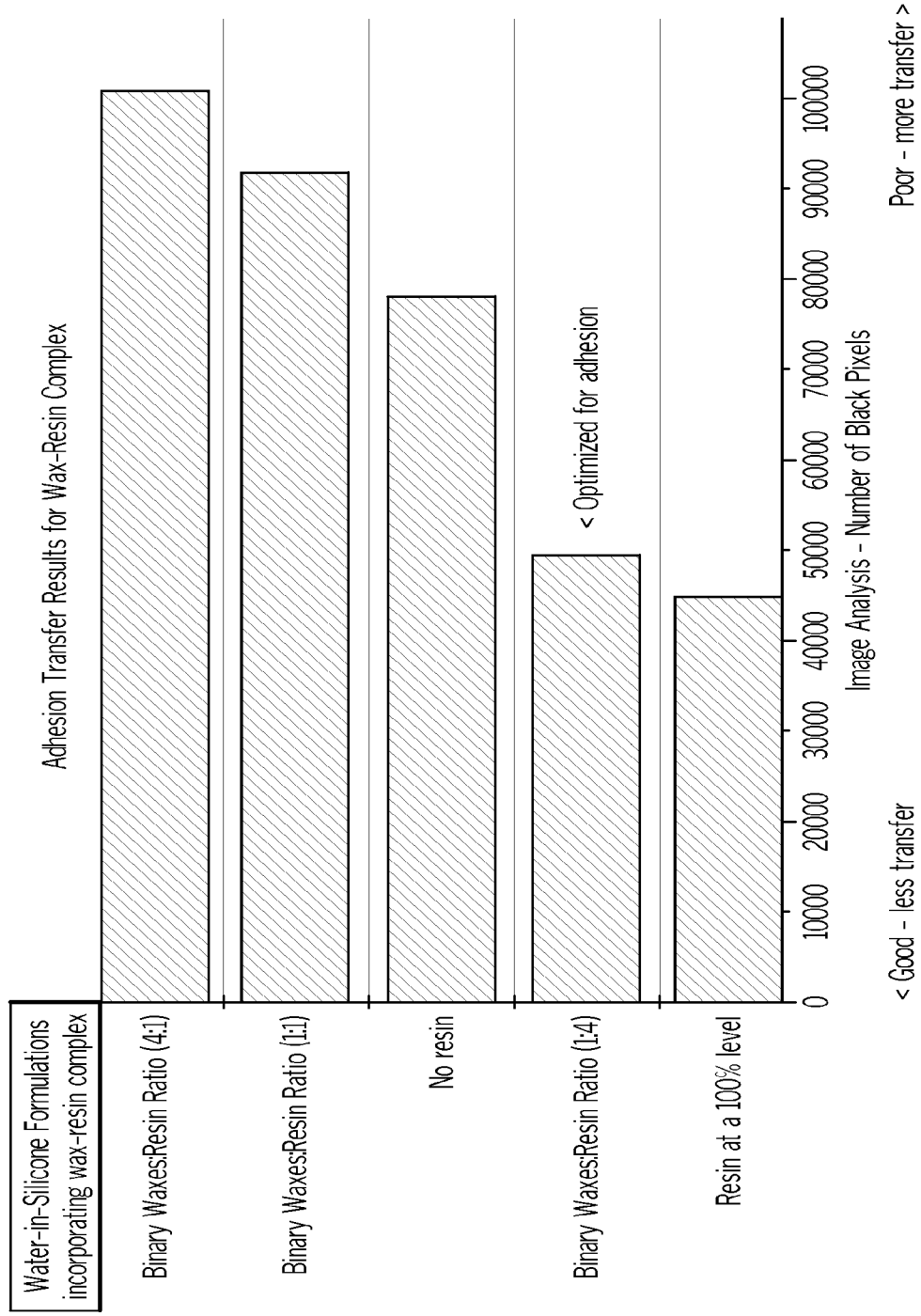
FIG. 2 is a graphical representation of adhesion transfer for a range of materials.

Films were created from a series of water-in-silicone/isododecane formulations containing pigments and a wax-resin composition in accordance with certain aspects of the present invention at various ratios or blends of the waxes and resin components. These films were pressed on adhesive tape at a constant pressure and weight, removed and then transferred to image analysis for results. This testing demonstrates the varying degrees for strength of adhesion of the films incorporating the wax: resin complexes and leads to optimization of the invention. Results are shown in FIG. 2.

Test Results for Gloss

Films were created from a series of water-in-silicone/isododecane formulations containing pigments and a wax-resin composition in accordance with certain aspects of the present invention at various ratios or blends of the waxes and resin components. These films were then measured with a gloss meter. This testing demonstrates the synergy of combining specific waxes in combination with the resin to improve gloss of finished products. Results are in Table 1. Increasing gloss number indicates higher gloss.

Results were as follows:

TABLE 1

| Water-in-Silicone Formulations incorporating wax-resin complex | Gloss Results for Wax-Resin Complex |
| --- | --- |
| No resin | 1.05 |
| Resin at a 100% level | 1.06 |
| Binary Waxes:Resin Ratio (1:4) | 1.52 (Optimized) |
| Binary Waxes:Resin Ratio (1:1) | 1.32 |
| Binary Waxes:Resin Ratio (4:1) | 1.37 |

In accordance with the invention, a hydrocarbon resin, hydrogenated polycyclopentadiene, can be blended (either individually, or in binary and ternary blends) of waxes that are 1) hydrocarbon-based (such as paraffin, ozokerite, microcrystalline and synthetic waxes, polyethylene, etc.), 2) hydrocarbon waxes modified with silicone (such as alkyl silicone waxes) or fluoro moieties, 3) silicone or fluoro waxes, 4) natural waxes that contain high levels of hydrocarbons (such as candelilla, beeswax, carnauba, etc.), 5) hydrogenated natural waxes or modified versions thereof, 6) synthetic waxes such as Fischer-Tropsch waxes or amide waxes, ester waxes, etc., or 7) the composite materials described herein may be prepared by various processes including, without limitation, by 1) recrystallization from a molten mixture of solid waxes or polymeric waxes and a solid hydrocarbon resin, 2) recrystallization from a molten mixture of solid waxes or polymeric waxes and a partially solvated hydrocarbon resin, or 3) recrystallization from a molten mixture of solubilized waxes or polymeric waxes and a fully solubilized hydrocarbon resin.

In accordance with the invention, solid composite wax-resin that is powdered, flaked, prilled, molded or extruded is produced.

Waxes (individually or in combinations) may be incorporated in a range of about 2 to about 98% by weight. The hydrocarbon resin may range from about 2% to about 98% by weight In accordance with the invention, 1 to 99% hydrogenated polycyclopentadiene may be dissolved in 1 to 99% wax which is processed at or above the temperatures of the softening point of the resin.

In a solvent based process, 10 to 90% hydrogenated polycyclopentadiene is dissolved in volatile hydrocarbon (1 to 50 parts) which is added to molten wax at a level of 10 to 90% and processed at or below the softening point of the resin.

The solvent process of the invention yields solid/resin wax composites that are easier to process, melting at around 50° C.-60° C., as compared to resin which softens around 100° C.

Even very small amounts of solid waxes significantly modified the properties of hydrogenated polycyclopentadiene with regards to flexibility and other properties and vice-versa. Depending upon the ratio of waxes, in accordance with certain embodiments, the waxes were able to modify the polycyclopentadiene to improve its structure and decrease its tack. Thick films of hydrogenated polycyclopentadiene remain tacky indefinitely while thin films of the material are brittle, in accordance with certain embodiments. The addition of waxes to the substance improved both thick and thin films. Similarly the hydrogenated polycyclopentadiene could be modified with the waxes to form new, malleable structures that could be drawn out like filaments.

Very small levels of waxes in ratio to the polymer formed a composite material having similar properties to standard accepted cosmetic materials such as polybutene and polyisobutene, etc. Higher levels of waxes in ratio to the polymer resulted in new materials with unique properties for cosmetics and pharmaceuticals.

Wax-Resin Composite Formulas_Produced Via a Solvent and Thermal Process

Throughout this specification, the amount of ingredients by weight are referenced to the weight of the total composition, unless otherwise specified. The following examples illustrate the invention.

Thermal Process

| CRYSTALLINE SOLID FORM-THERMAL PROCESS INGREDIENTS | |
| --- | --- |
| EXAMPLE 1. [Total 100 parts] (Resin/Antioxidant Phase) | |
| Koboguard 5400 | 79.70 |
| Covi-Ox T70 | 0.30 |
| | 80.00 |

CRYSTALLINE SOLID FORM-THERMAL PROCESS INGREDIENTS

(Wax Phase)

| | |
|---|---|
| Asensa SC210 | 13.34 |
| Carnauba Wax | 6.66 |
| | 20.00 |

EXAMPLE 2. [Total 100 parts]
*(Resin/Antioxidant Phase)*

| | |
|---|---|
| Escorez 5415 | 49.70 |
| Covi-Ox T50 | 0.30 |
| | 50.00 |

(Wax Phase)

| | |
|---|---|
| Microcrystalline Wax | 33.34 |
| Candelilla Wax | 16.66 |
| | 50.00 |

EXAMPLE 3. [Total 100 parts]
*(Resin/Antioxidant Phase)*

| | |
|---|---|
| Escorez 5415 | 79.67 |
| Rosemary Oleoresin | 0.33 |
| | 80.00 |

(Wax Phase)

| | |
|---|---|
| Asensa SC 810A | 13.34 |
| Ceresin Wax | 6.66 |
| | 20.00 |

EXAMPLE 4. [Total 100 parts]
*(Resin/Antioxidant Phase)*

| | |
|---|---|
| Escorez 5400 | 59.66 |
| Rosemary Oleoresin | 0.33 |
| | 60.00 |

(Wax Phase)

| | |
|---|---|
| Performa V103 | 26.66 |
| Ceresin Wax | 13.34 |
| | 40.00 |

Thermal Process Procedure

The following procedure is used in examples 1-4

1. Tare (weigh) a 1200 ml stainless steel beaker. Put the resin and antioxidant into the beaker. under a fume hood. Alternatively, an explosion-proof mixer under the fume hood may be used. Fill a bain marie (water bath—2000 ml SS beaker) with 50/50 propylene glycol/tap water mixture or a bath of mineral oil.
2. Immerse the 1200 ml SS beaker into the bath. The bath should be heated to 105° C. to 110° C. Do not allow the batch to exceed a temperature of 120° C. Temperature may be monitored directly using a thermometer immersed in the melted resin. Monitor the batch at all times during preparation.
3. Be sure the 1200 ml stainless steel beaker is completely immersed in the bath up to the level of the resin.
4. After the resin is melted (approximately 105° C.), add the waxes, which are at room temperature, to the beaker. Heat to achieve a temperature close to but not above 120° C. Take care to ensure that the level of materials in the beaker is not above the level of the bath.
5. Cover the beaker with aluminum foil during the heating process.
6. Allow the blend to melt almost completely which occurs at a temperature in the range of 110-120° C. Once this temperature has been achieved, and almost complete melting observed, start to mix with a stirrer. The softening/melting process may take 60-90 minutes to complete. The softened resin will solubilize in the other materials as stirring is begun.
7. When the solution appears clear begin stirring slowly with a Caframo or Lightnin' mixer until the polymer is solubilized. Solubilization of the polymer may be determined by observing the clarity of the solution and which should be transparent as opposed to cloudy.
8. After the solution has been stirred to melt all solids and is homogenous continue slow stirring for an additional 15 minutes. The object of this additional staring is to remove air from the product.
9. Record weight of the beaker and product.
10. Pour the batch into silicone or teflon enamel coated molds or pans. Cover with aluminum foil.
11. Allow the melt to solidify at room temperature. Record weight or batch yield.

Solvent Process

As an alternative to the thermal process described above, in accordance with the invention, the crystalline solid composite wax-resin matrices may be made by a solvent process.

Crystalline Solid Form

Produced by the Solvent Process

EXAMPLE 5. [Total 120 parts]
*(Solvent/Antioxidant Phase)*

| | |
|---|---|
| Shell Sol OMS | 19.67 |
| Covi-Ox T70 | 0.33 |
| | 20.00 |

(Wax-Resin Phase)

| | |
|---|---|
| Escorez 5400 | 80.00 |
| Asensa SC210 | 13.34 |
| Carnauba Wax | 6.66 |
| | 100.00 |

EXAMPLE 6. [Total 120 parts]
*(Solvent/Antioxidant Phase)*

| | |
|---|---|
| Isopar C | 19.67 |
| Covi-Ox T50 | 0.33 |
| | 20.00 |

(Wax-Resin Phase)

| | |
|---|---|
| Escorez 5380 | 50.00 |
| Microcrystalline Wax | 33.34 |
| Candelilla Wax | 16.66 |
| | 100.00 |

EXAMPLE 7. [Total 120 parts]
*(Solvent/Antioxidant Phase)*

| | |
|---|---|
| Isododecane | 19.67 |
| Rosemary Oleoresin | 0.33 |
| | 20.00 |

(Wax-Resin Phase)

| | |
|---|---|
| Escorez 5415 | 80.00 |
| Performa V103 | 13.34 |
| Ceresin Wax | 6.66 |
| | 100.00 |

-continued

EXAMPLE 8. [Total 120 parts]
(Solvent/Resin/Antioxidant Phase)

| | |
|---|---|
| K5400IDD (Kobo) | 77.67 |
| Rosemary Oleoresin | 0.33 |
| | 78.00 |
| (Wax Phase) | |
| Performa V103 | 28.00 |
| Ceresin Wax | 14.00 |
| | 42.00 |

Solvent Process

Laboratory Procedure

Examples 5-8 are made using the following process

1. Tare (weigh) a 1200 ml stainless steel beaker. Put antioxidant and solvent into beaker under a fume hood. Use an explosion-proof mixer under the fume hood. Fill a bain marie (water bath—2000 ml stainless steel beaker) with tap water. Slowly begin heating.
2. Immerse the 1200 ml stainless steel beaker into the bath. Do not allow the batch to exceed a temperature of 100° C. at any time. Monitor the batch at all times during preparation for safety reasons, as temperature exceeds the flashpoint of the solvent.
3. Be sure the 1200 ml stainless steel beaker is completely immersed in the steam bath up to the level of where the liquid and waxes are present.
4. Do not cover the beaker with aluminum foil. Weigh and add, waxes and the resin which are at room temperature, at about 30-35° C., and begin heating to 90-95° C. in the water bath. Record weight of the beaker and product to monitor the extent to which the solvent has been boiled off.
5. When the solution appears clear begin stirring slowly with a dispersator.
6. Increase the dispersator speed and continue stirring until all of the solvent has evaporated which is determined via weight measurements.
7. Pour the batch into silicone or teflon enamel coated molds or pans. Cover with aluminum foil.
8. Allow the melt to solidify at room temperature. Record weight or batch yield.

Cosmetic Product Application Examples

The wax-resin composite materials manufactured in accordance with examples 1-8 above, may be used to make a wide variety of cosmetic products.

In making the various cosmetic products illustrated by the following examples, any of the composites whose fabrication is explained in connection with the above Examples 1-8, may be used, although different characteristics in feel, fluidity, etc. may be noted. Particular ones of the Examples 1-8 with particular waxes and/or other ingredients may be suggested below. Moreover, combinations of the Example 1-8 products in a wide range of proportions is expected to yield products with excellent characteristics. In this application, the convention of listing ingredients and the process of mixing the same is followed. CFTA nomenclature (e.g. (and)) is also sometimes used herein.

Example 9

Cosmetic O/W Mascara Incorporating the Wax-resin Composite

Example of a Wax (Oil)-in-water Emulsion Product

| | Ingredients | | |
|---|---|---|---|
| Phase I | Deionized Water | 47.65 | |
| | Natrosol 250HR | 0.80 | (gum stabilizer) |
| | Methylparaben | 0.20 | (preservative) |
| | Butylene Glycol | 3.00 | (humectant/plasticizer) |
| Phase II | Ammonium Hydroxide (30% Solution) | 0.35 | (neutralizing agent) |
| Phase III | Hydrogenated Polycyclopentadiene (and) Polyethylene (and) Ozokerite (and) Tocopherol | 3.00 | (or any products of Ex. 1-8) |
| | Stearic Acid | 2.00 | (emulsifier) |
| | Synthetic Bayberry Wax | 1.50 | (emollient wax) |
| | White Beeswax | 3.00 | (thickener) |
| | Lanolin USP | 1.00 | (emulsifier) |
| | C18-36 Triglycerides | 3.50 | (stabilizer/thickener) |
| Phase IV | Black NF (black iron oxide) | 8.00 | (colorant) |
| | Silica - MSS500W (Kobo) | 3.00 | (textural agent) |
| Phase V | Daitosol 5000AD Emulsion Latex (Daito) | 22.00 | (film-former) |
| Phase VI | Germaben II/ISP (a preservative) (ISP) | 1.00 | (preservative) |
| | | 100.00 | |

Process:
1. Prepare this entire batch under a fume hood and with appropriate respirator and cartridges for working with ammonia. Except where specified otherwise, materials are at room temperature. Add the aqueous Phase I to a 2000 ml stainless steel beaker and begin mixing with propeller agitation. After mixing for 10 minutes, begin heating to 90 C in a water bath covering the beaker with aluminum foil.
2. Keep ammonium hydroxide refrigerated and at a temperature of approximately 5-10° C. The 'refrigerated' aqueous ammonia Phase II should not be added until just prior to emulsification in Step 3 to avoid the ammonia volatilizing off.
3. In a separate beaker, combine Phase III (one of the wax-resin composites of Examples 1-8 and other waxes) at room temperature and then heat to 90 C.
4. When both phases (I and III) are at temperature (90 C), add Phase II ammonia very slowly to Phase I, keeping the beaker covered as much as possible with aluminum foil.
5. Then add Phase III to the aqueous mixture of Phase I and Phase II. Continue mixing with propeller agitation and maintain temperature at 90° C. for 15 minutes keeping the beaker covered. Propeller agitation may be done with a Lightnin mixer.
6. Phase IV powders should be pulverized to a size of, for example, about 30-2000 nm, or in the case of other pigments as large as about 5000 nm. Sift the powders into the heated batch while continuing to mix with propeller agitation. Once powders are completely added, switch from propeller mixing to homogenization. Homogenization may be done with a conventional homogenizer such as a Silverson. Homogenize until pigment is completely dispersed. Once pigment is fully dispersed, change back to propeller agitation. Begin air cooling with continued propeller agitation. Air cooling may be done by removing the beaker from the bath.

7. Add the emulsion latex (Phase V) to the batch after the temperature drops to about 60-65 C.
8. Allow the batch to cool to about 55° C. and weigh, noting weight loss as compared to starting materials and add Q.S. to compensate for the water loss measured at 55 C.
9. When batch has cooled to 50 C, add the preservatives (Phase VI) and continue stirring.
10. Cool to 25-30 C. Put product into mascara bottles and seal.

Example 10

Pharmaceutical Sunscreen Using the Wax-Resin Composite

Example of Water-in-oil Emulsion Product

| | Ingredients: | % Wt. | |
|---|---|---|---|
| PHASE 1 | Optinally, for example, Polyethylene (and) Carnauba Wax (and) Hydrogenated Polycyclopentadiene (and) Tocopherols or combinations) | 7.00 | (or products of examples 1-8 |
| | Permethyl 99A | 7.79 | (solvent) |
| PHASE 2 | Lucentite SAN-P | 2.00 | (thickener/stabilizer) |
| | Phenoxyethanol | 0.66 | (preservative) |
| PHASE 3 | PM9P50M170 Titanium Dioxide (and) Isododecane (and) Alumina (and) Methicone (and) Polyhydroxystearic Acid | 30.00 | (inorganic sunscreen agent pigment Titanium Dioxide dispersion) |
| | Tospearl 2000B | 3.38 | (spherical powder to improve application) |
| | Cyclomethicone and PEG/PPG-20/15 Dimethicone | 6.80 | (surfactant/primary emulsifier) |
| PHASE 4 | Sorbitan Oleate | 0.75 | (secondary emulsifier) |
| | Sorbitan Isostearate | 0.75 | (secondary emulsifier) |
| | Propylparaben | 0.10 | (preservative) |
| PHASE 5 | Sodium Chloride | 1.00 | (emulsion stabilizer) |
| | Deionized Water | 17.70 | (solvent) |
| | Methylparaben | 0.10 | (preservative) |
| PHASE 6 | Glyceryl Tribeheante | 1.65 | (thickener) |
| | Synthetic Beeswax | 1.10 | (thickener) |
| | dl-alpha Tocopherol | 0.10 | (antioxidant) |
| PHASE 7 | Velvesil 125 (GE) | 17.70 | (texture modifier) |
| PHASE 8 | Vanillin FCC | 0.02 | (fragrance) |
| | Phenoxyethanol USP | 0.10 | (preservative) |
| PHASE 9 | Deionized water | 1.00 | (solvent/carrier) |
| | dl-Panthenol | 0.30 | (vitamin) |
| *TOTALS: | | 100.00 | |

Example 12

Personal Care Antiperspirant Incorporating Inventive Wax-Resin Composite

Ternary Example of an Anhydrous Product

| Ingredients: | % Wt. |
|---|---|
| Permethyl 99A (isododecane) (solvent) | 41.00 |
| Hydrogenated Polycyclopentadiene and Synthetic Wax and Carnauba and Tocopherols (or product of examples 1-8) | 5.00 |
| Summit AZG-370 (Summit) (aluminum zirconium tetrachlorohydrex glycine) (active antiperspirant agent) | 25.00 |
| Lanette Wax 18 (Henkel) (stearyl alcohol) (structural agent) | 16.00 |
| Castorwax MP80 (CasChem) (hydrogenated castor oil) (structural agent) | 5.00 |
| Dow Corning 9040 (cyclomethicone (and) dimethicone Crosspolymer) (polymeric textural agent) | 8.00 |
| | 100.00 |

Procedure:
1. Add all ingredients (wax-resin composite, solvent, waxes, etc.) to a 600 ml stainless steel beaker. Cover the beaker with aluminum foil.
2. Mix at ambient temperature with a propeller mixer in a water bath until all materials are dispersed evenly.
3. Begin heating to 70-80° C. by heating of the water bath while mixing. After all waxes have melted to produce a uniform solution, remove the batch from the heat source, for example by removing it from the water bath. Continue to mix.
4. When the temperature of the solution reaches 60° C., pour into antiperspirant containers. Allow to cool to ambient temperature.

Example 13

Cosmetic O/W Eyeliner Incorporating the Wax-Resin Composite

Quaternary Example of Wax Oil-in-water Emulsion

| Formula: | % Wt. | |
|---|---|---|
| Phase A | | |
| Deionized water | 61.05 | (solvent) |
| Phase B | | |
| Xanthan gum | 0.50 | (stabilizer) |
| Carboxymethyl cellulose | 0.40 | (stabilizer) |
| Magnesium aluminum silicate | 0.40 | (suspending agent) |
| Phase C | | |
| Deionized water | 12.00 | (solvent) |
| PVP K30 | 8.00 | (film-former) |
| Phase D | | |
| Iron oxides (black) | 6.50 | (colorant) |
| Phase E | | |
| Lecithin | 0.20 | (wetting agent) |
| Triethanolamine, 99% | 1.00 | (emulsifier) |
| Methylparaben | 0.35 | (preservative) |

-continued

| Formula: | % Wt. | |
|---|---|---|
| Phase F | | |
| Stearic acid | 2.50 | (emulsifier) |
| Hydrogenated Polycyclopentadiene and Polyethylene and Beeswax and Paraffin Wax and Tocopherols | 5.00 | (or any products of Ex. 1-8) |
| Sorbitan sesquioleate | 1.00 | (emulsifier) |
| Phase G | | |
| Deionized water | 1.00 | (solvent) |
| Imidazolidinyl urea | 0.10 | (preservative) |
| | 100.00 | |

Procedure:
1. Put the phase A water into a stainless steel beaker. Heat the water (Phase A) to 85° C. using a water bath.
2. Dry blend the phase B ingredients (which are polymer gums) and add to A using a propeller mixer at medium/high speed. Mix until the gums are completely hydrated., approximately 15-20 minutes.
3. Prepare Phase C by mixing the PVP K30 film former with the deionized water of Phase C in the separate stainless steel beaker at room temperature and then add the mixture to the batch formed by the mixture of Phase A and Phase B.
4. Add the pigments (Phase D) slowly to the batch until a substantial amount of dispersion has occurred, and then mill the entire batch for 5 minutes at a gap setting of 20 using a colloid mill.
5. Pour the output of the colloid mill into a stainless steel beaker. Add the ingredients of phase E (triethanolamine, lecithin, methylparaben) to the batch, heating to 75-80° C., using a water bath to heat the same and form a heated main batch.
6. Mix phase F ingredients (wax-resin composite, and emulsifiers) separately and heat to 80-85° C. using a water bath with stirring using a propeller mixer to make a Phase F blend. Slowly add the phase F blend to the main batch and mix for 15 minutes. Begin air cooling by removing the heat source. Cool to 40-45° C.
7. Mix the preservative phase (Phase G) until uniform by hand stirring in a separate beaker to form a Phase G mixture. Add the Phase G mixture to the batch, and continue mixing and begin force cooling with ice and water bath to 30° C. Package into appropriate vials.

Example 14

Cosmetic Lip Gloss Incorporating the Wax-Resin Composite

Quaternary Example of an Anhydrous Product

| Ingredients: | % Wt. |
|---|---|
| Hydrogenated Polycyclopentadiene and Ceresin Wax (or other products of examples 1-8) and Candelilla Wax and Paraffin Wax and Tocopherols | 10.00 |
| Permethyl 102A (solvent) | 71.50 |
| Ceraphyl 368 (ISP) (octyl palmitate) (emollient) | 10.00 |
| Ceraphyl 55 (ISP) (tridecyl neopentanoate) (emollient) | 5.00 |
| Prisorine 2039 (Uniqema) (isostearyl isostearate) (spreading agent) | 3.00 |

-continued

| Ingredients: | % Wt. |
|---|---|
| LiquiPar Oil (ISP) (isopropylparaben (and) isobutylparaben (and) butylparaben) (preservative) | 0.50 |
| | 100.00 |

Procedure:
1. Mix all ingredients (wax-resin composite, oils, esters, preservative, etc.) at room temperature in a 250 ml stainless steel beaker using a Caframo mixer.
2. Heat the batch slowly to 70-75° C. in a water bath with slow stirring using a Caframo propeller stirrer until the mixture is uniform.
3. Once the batch appears homogenous, allowed to cool to 45° C., by removing beaker from heated water bath, and add flavor and color if desired.
4. Package into appropriate containers.

Example 15

Cosmetic Eyeliner Pencil Incorporating the Wax-Resin Composite

Ternary Example of an Anhydrous Product

| Ingredients: | | % Wt. |
|---|---|---|
| Permethyl 102A | (solvent) | 49.50 |
| Hydrogenated Polycyclopentadiene and Polyethylene and Carnauba and Tocopherols | (or any product of examples 1-8) | 10.00 |
| Ozokerite | (gelling agent) | 12.00 |
| Polyethylene | (gelling agent) | 4.00 |
| Carnauba | (structural agent) | 3.50 |
| Stearyl Alcohol | (emollient) | 2.00 |
| Beeswax | (thickener) | 5.00 |
| Titanium Dioxide 35/65 pre-ground slurry | (colorant) | 2.00 |
| Ultramarine Blue 35/65 pre-ground slurry | (colorant) | 12.00 |
| | | 100.00 |

Procedure:
1. Add all ingredients (wax-resin composite, solvent, additional waxes, colors, etc.) to a 600 ml stainless steel beaker in a water bath.
2. Mix using a propeller stirrer at ambient temperatures until all materials are dispersed evenly. Begin heating to 85° C. and continue mixing.
3. Once all the waxes have melted to produce a uniform dispersion, remove the batch from the heat source. Immediately fill the batch into stainless steel containers. After product has sufficiently cooled, extrude into pencil form.

Example 16

Cosmetic Mascara Incorporating the Wax-resin Composite

Ternary Example of a Water-in-oil Product

| Phase 1. | | |
|---|---|---|
| Hydrogenated Polycyclopentadiene (and) Carnauba Wax and Polyethylene | 12.00 | (or any product of examples 1-8) |

-continued

| | | |
|---|---|---|
| (and) Tocopherols | | |
| Isododecane | 42.73 | (solvent) |
| Phase 2. | | |
| Lucentite SAN-P | 2.00 | (thickener/stabilizer) |
| Ethyl Alcohol 39C | 1.00 | (polar additive) |
| Phase 3. | | |
| Black Iron Oxide | 5.00 | (colorant) |
| Cyclomethicone (and) PEG/PPG-20/15 Dimethicone | 5.00 | (emulsifier/ surfactant) |
| Phase 4. | | |
| Black 2WBG45 (Carbon Black (and) Butylene Glycol (and) Water) | 5.00 | (dispersed colorant) |
| Deionized Water | 15.00 | (solvent) |
| Sodium Chloride | 0.25 | (stabilizer) |
| Phase 5. | | |
| C18-36 Triglycerides | 5.00 | (thickener) |
| White Beeswax | 6.00 | (thickener) |
| Phase 6. | | |
| Phenoxyethanol, Methylparaben, Propylparaben & Ethylparaben | 1.00 | (preservative) |
| Vanillin USP | 0.02 | (fragrance) |
| | 100.00 | |

Procedure:

1. Combine Phase 1 materials (wax-resin composite and solvent) and heat to 70° C. in a water bath.
2. Add the Lucentite SAN-P (suspending/stabilizer) from Phase 2 slowly to Phase 1. Stir with a dispersator in a 600 ml stainless steel beaker at high speed for 20 minutes. Add the ethanol from Phase 2 and stir an additional 20 minutes. Gel formation should take place which leads to a thickening of the main batch.
3. Separately combine the emulsifier and black iron oxide of Phase 3 together to make a Phase 3 mixture and stir for 10 minutes using a dispersator. Then add the Phase 3 mixture to the main batch. Continue heating to 80-85 C.
4. Separately combine the ingredients of Phase 4 with a propeller mixer and then heat to 80-85 C while continuing to mix with a propeller mixer. After the ingredients in the Phase 4 mixture are well mixed, add the Phase 4 mixture thus produced) very slowly to the main batch and stir at high speed with a dispersator for 45 minutes, maintaining the temperature at 80-85° C.
5. Combine the triglycerides and wax of Phase 5 in a separate beaker, heating with a water bath to 80° C. to form a Phase 5 mixture. Add the Phase 5 mixture to the main batch and continue to disperse while heating to 85-87° C.
6. Begin air cooling, for example by removing the hot water bath and allowing the main batch to cool.
7. At 65° C., take the weight of the main batch and add Isododecane to make up for solvent loss. Force cool with an ice bath to 42° C.
8. At 42° C. add Phase 6, the preservatives and vanillin.
9. Continue mixing and cool to 25° C. Fill into appropriate containers.

Example 17

Cosmetic Face Powder Incorporating the Wax-Resin Composite

Ternary Example of a Cosmetic Powder

| Ingredient Listing | | |
|---|---|---|
| Part A. | | |
| Mica (and) Isopropyl Titanium Triisostearate (GMS-I2) | 62.27 | (base powder component) |
| Yellow Iron Oxide(and) Isopropyl Titanium Triisostearate (BYO-I2) | 0.24 | (colorant) |
| Red Iron Oxide (and) Isopropyl Titanium Triisostearate (BRO-I2) | 0.24 | (colorant) |
| Methylparaben | 0.15 | (preservative) |
| Part B. | | |
| Hydrogenated Polycyclopentadiene (and) Carnauba Wax and Polyethylene (and) Tocopherols | 4.00 | (or any product of Exs. 1-8) |
| Pentaerythritol Tetraoctanoate | 4.50 | (emollient binder) |
| Dimethicone(and)Trimethyl Siloxy Silicate | 18.60 | (binder) |
| Silica MSS-500/3H | 10.00 | (soft focus/optical agent) |
| | 100.00 | |

Procedure:
1. Combine the ingredients of Part A and mix thoroughly with a spatula.
2. Pass the premixed Part A pigment phase through a pulverizer or blender until the color is fully extended.
3. Mix the binder ingredients of Part B) in a beaker and put the beaker in a heated water bath. Pre-blend the binder phase (Part B) heating to 70-75° C. in a small stainless steel beaker with a propeller-type mixer until the wax-resin composite is dissolved.
4. Spray or add the binder (Part B) in very small increments to Part A slowly, mix, and pass through a pulverizer or blender until oil and wax-resin composite is dispersed.
5. Press into cakes in appropriate pans and package.

What is claimed is:

1. A process for making a pharmaceutical or cosmetic composition, comprising the steps of:
    (a) making a solid wax-resin composite wherein said making of said solid wax resin composite comprises combining:
        (i) hydrogenated polycyclopentadiene
        (ii) a wax, wherein said wax comprises at least one abhesive wax having a melting point range of 55° C. to about 115° C.,
    (b) processing the solid wax-resin composite into powder, granules, prills, flakes or other particulates; and
    (c) blending said wax-resin composite into a pharmaceutical or cosmetic composition.
2. The process according to claim 1 wherein the wax-resin composite is pumped through a pastillator, forming transparent solid pastilles.

3. The process according claim 1, wherein the wax comprises a first wax, said first wax being a synthetic wax having a melting point of about 55° C. to about 115° C.; and a second wax as a blending agent, said second wax comprising a natural wax containing hydrocarbons to provide miscibility, and wherein said second wax has a lower melting point than the first wax.

4. The process according to claim 3, wherein the first wax is polyethylene and the second wax is Carnauba wax.

5. A process according to claim 1 wherein the hydrogenated polycyclopentadiene having a refractive index of 1.55-1.57.

6. A process for making a cosmetic composition comprising the steps of:
  (a) at least partially solvating hydrogenated polycyclopentadiene in a solvent under the application of heat in the range of 80-85° C. resulting in a resin-solvent blend;
  (b) preparing a composition of wax, wherein said wax comprises at least one abhesive wax having a melting point range of 55° C. to about 115° C.;
  (c) mixing said resin-solvent blend and said wax to form a wax-resin blend;
  (d) removing the solvent from said wax-resin solution to produce a solid wax-resin composite; and
  (e) blending said wax-resin composite with materials selected from the group consisting of pigments, pharmaceuticals, oils, esters and sunscreens.

7. A method for producing a solid wax-resin composite comprising:
  (a) melting hydrogenated polycyclopentadiene resin;
  (b) blending together the melted hydrogenated polycyclopentadiene resin with waxes at a temperature sufficient to melt the waxes, said wax comprising at least one of a first wax selected from the group consisting of crystalline polyethylene waxes, synthetic waxes, hydrocarbon waxes, petroleum waxes and mixtures thereof, and a second wax selected from the group consisting of natural or synthetic waxes containing hydrocarbons or hydrocarbon-like structures;
  (c) allowing the blended hydrogenated polycyclopentadiene resin and waxes to solidify into a wax-resin composite; and
  (d) post-processing the wax-resin composite to form slabs, pastilles, flakes or other solid forms.

8. A method as in claim 7 wherein the hydrogenated polycyclopentadiene resin has a refractive index of 1.55-1.57.

9. A method as in claim 8, wherein said temperature sufficient to melt the waxes is below 125° C.

10. A method as in claim 9, wherein said post processing includes mechanically breaking up said solidified blended hydrogenated polycyclopentadiene resin and waxes.

11. A method as in claim 10, wherein the hydrogenated polycyclopentadiene resin is melted with an antioxidant.

12. A method as in claim 11, wherein the antioxidant comprises tocopherols.

* * * * *